(12) United States Patent
Hong et al.

(10) Patent No.: US 11,993,552 B2
(45) Date of Patent: May 28, 2024

(54) METHOD AND DEVICE FOR CONTINUOUSLY SYNTHESIZING CYCLOPROPANE COMPOUNDS

(71) Applicant: ASYMCHEM LABORATORIES (TIANJIN) CO., LTD., Tianjin (CN)

(72) Inventors: Hao Hong, Morrisville, NC (US); Jiangping Lu, Tianjin (CN); Xichun Feng, Tianjin (CN); Xingfang Sun, Tianjin (CN); Feng Zhang, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 90 days.

(21) Appl. No.: 17/622,294

(22) PCT Filed: Jul. 2, 2019

(86) PCT No.: PCT/CN2019/094345
§ 371 (c)(1),
(2) Date: Dec. 23, 2021

(87) PCT Pub. No.: WO2021/000248
PCT Pub. Date: Jan. 7, 2021

(65) Prior Publication Data
US 2022/0242805 A1    Aug. 4, 2022

(51) Int. Cl.
*C07C 2/86* (2006.01)
*C07B 37/02* (2006.01)

(52) U.S. Cl.
CPC ............... *C07C 2/86* (2013.01); *C07B 37/02* (2013.01); *C07C 2601/02* (2017.05)

(58) Field of Classification Search
None
See application file for complete search history.

(56) References Cited

U.S. PATENT DOCUMENTS 5,854,405 A    12/1998 Archibald
2016/0280615 A1*    9/2016 Schroeder ............. C07C 49/553

FOREIGN PATENT DOCUMENTS

| CN | 101633620 | 1/2010 |
|----|-----------|--------|
| CN | 105418452 | 3/2016 |
| CN | 105658604 | 6/2016 |
| CN | 107382725 | 11/2017 |

(Continued)

OTHER PUBLICATIONS

Final Rejection issued in JP.
Office Action in issued in JP.
Supplementary European Seach Report for EP 19936457.

*Primary Examiner* — Ali Z Fadhel
(74) *Attorney, Agent, or Firm* — Riverside Law LLP

(57) ABSTRACT

The present disclosure discloses a method and a device for continuously synthesizing cyclopropane compounds. The method includes the following steps: continuously performing a synthetic reaction of a diazomethane precursor in a first reactor, the reaction product of the first reactor flowing into a separator for stratification, the organic phase obtained by stratification overflowing into a second reactor, continuously consuming the diazomethane precursor in a second reactor to prepare diazomethane and performing an electron-rich monoolefin cyclopropanation reaction in situ so as to obtain the cyclopropane compound.

17 Claims, 1 Drawing Sheet

(56) References Cited

FOREIGN PATENT DOCUMENTS

| | | |
|---|---|---|
| JP | 1999209330 | 3/1999 |
| JP | 2016538335 | 12/2016 |
| JP | 2018527373 | 9/2018 |
| WO | 2015059290 | 4/2015 |
| WO | 2019094143 | 5/2019 |

* cited by examiner

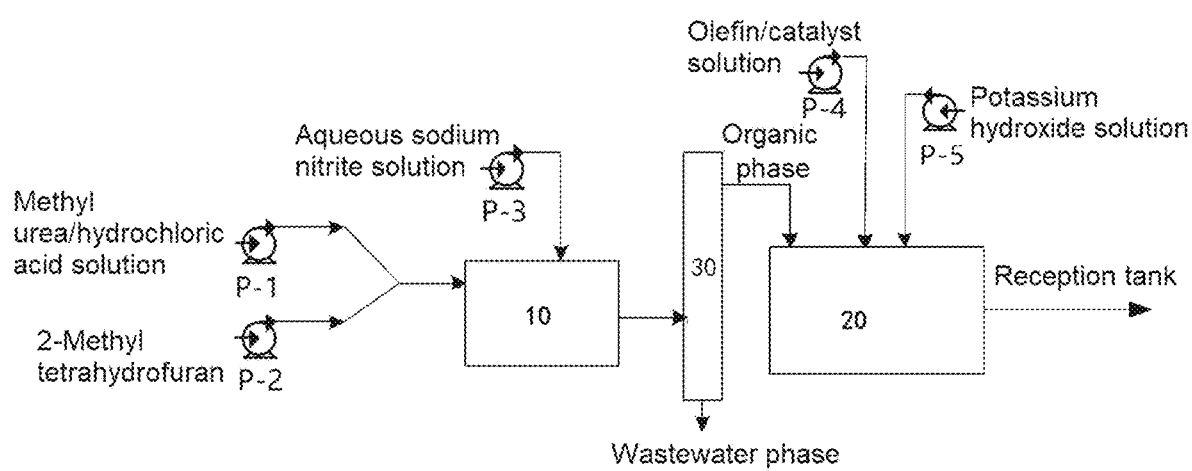

METHOD AND DEVICE FOR CONTINUOUSLY SYNTHESIZING CYCLOPROPANE COMPOUNDS

CROSS-REFERENCE TO RELATED APPLICATIONS

This application is a U.S. National Phase application filed under 35 U.S.C. § 371 claiming benefit to International Patent Application No. PCT/CN2019/094345, which was filed on Jul. 2, 2019, the entire contents of which are incorporated herein by reference in its entirety.

TECHNICAL FIELD

The present disclosure relates to the field of pharmaceutical and chemical industry, and in particular to a method and a device for continuously synthesizing a cyclopropane compound.

BACKGROUND

Due to tension force of a three-membered ring and unique double bond properties, cyclopropane compounds may participate in the construction of various heterocyclic compound frameworks. Lots of natural products and active ingredients are cyclopropane compounds or derived from cyclopropane compounds. Therefore, cyclopropane compounds have important application value in the field of pharmaceutical and chemical industry. It is a common method to synthesize cyclopropane compounds via the cyclopropanation of olefins.

Simmons-Smith reaction is a kind of reaction widely applied in the cyclopropanation of olefins. Diethyl zinc or zinc-copper, diiodomethane (or dibromomethane) produce a carbene intermediate, and the carbene intermediate is reacted with olefins to produce cyclopropane compounds. Such kind of reaction easily enlarges production and may obtain good yield. However, because the dosage of an organometallic reagent is subjected to chemometry, a large number of metal wastes will produce after the reaction, which increases environmental pollution and treatment cost of wastes.

It is a very effective approach to perform cycloaddition on olefins to synthesize cyclopropane compounds using a catalytic amount of transition metal to catalyze diazo compounds. In the presence of a transition metal compound, diazo compounds are very easily decomposed to form a metal carbene intermediate and release nitrogen. Metal carbene is reacted with an olefinic bond to generate cyclopropane products. Such kind of reaction theoretically only produces a by-product nitrogen and thus, has very high atom economy, thereby greatly reducing the postprocessing cost. Diazomethane is a kind of common diazo compound, and is used to synthesize an unsubstituted three-membered ring. But diazomethane is volatile and highly toxic, and has carcinogenicity. Compounds including diazomethane precursors are sensitive to light, high temperature, impact and friction, and may cause decomposing explosion. These factors restrict the large-scale application of diazomethane in conventional batch reaction.

In recent years, Hansjoerg Lehmann, et al. have carried out continuous preparation of a diazomethane precursor (MNU), continuous preparation and application of diazomethane solution, capable of significantly decreasing the separation and use risk of the diazomethane precursor and diazomethane. But the continuous reaction has a longer equipment chain and involves in the risk of pipeline transfer of diazomethane solution. Doris Dellinger, et al. have performed continuous preparation of diazomethane and simultaneously isolated pure diazomethane by means of a permeable membrane technology for in situ reaction with a substrate. The preparation and application of diazomethane are successfully achieved simultaneously and the equipment chain is shortened, but the method has a high manufacturing cost of permeable membrane, small production capacity, and cannot achieve large-scale application within a short time. Oleg M. Nefedov, et al. have achieved in situ cyclopropanation to electron-rich monoolefine (free of an obvious conjugated structure) by in-situ generation of diazomethane; such a way may be performed efficiently with a conventional palladium catalyst. Bill Morandi, et al. have made use of an improved Fe-based catalyst and a one-pot process to achieve the in-situ production of diazomethane and perform high-selectivity cyclopropanation on conjugated olefins. Such two studies depend on controlling the feeding of diazomethane precursors to achieve the generation of diazomethane and cyclopropanation reaction of olefins simultaneously in a two-phase system. If the feeding speed of the diazomethane precursor is too fast, the yield of diazomethane in unit time is higher, and the decomposition rate of diazomethane catalyzed by a catalyst accelerates, thus generating by-products, such as, ethylene; while too slow feeding speed may cause the precipitation of the catalyst to affect the catalytic activity; these factors increase the operation risk of diazomethane precursors.

To sum up, there are major disadvantages in the prior art below: 1) the continuous preparation of diazomethane precursors, continuous preparation and application of diazomethane solution are achieved to greatly decrease the separation and use risk of the diazomethane precursor and diazomethane, but the continuous reaction has a longer equipment chain and involves in the risk of pipeline transfer of diazomethane solution; 2) for the preparation of diazomethane by continuous reaction, the separation of diazomethane with a permeable membrane may achieve the in situ reaction of diazomethane and substrate, but the method has a high manufacturing cost of permeable membrane, small production capacity, and cannot achieve large-scale application within a short time; 3) the one-pot process in batches achieves the generation of diazomethane and cyclopropanation reaction of olefins simultaneously, but the process increases the operation risk of diazomethane precursors.

SUMMARY

The present disclosure aims at providing a method and a device for continuously synthesizing a cyclopropane compound, thus avoiding the risk of pipeline transfer of diazomethane solution.

To achieve the above objective, according to one aspect of the present disclosure, provided is a method for continuously synthesizing a cyclopropane compound. The method includes the following steps: continuously performing a synthetic reaction of a diazomethane precursor in a first reactor, the reaction product of the first reactor flowing into a separator for stratification, the organic phase obtained by stratification overflowing into a second reactor, continuously consuming the diazomethane precursor in a second reactor to prepare diazomethane and performing an electron-rich monoolefin cyclopropanation reaction in situ so as to obtain the cyclopropane compound.

Further, the first reactor is a helical tube reactor or a continuous stirred tank reactor; and the second reactor is a continuous stirred tank reactor or a column reactor.

Further, a temperature of the first reactor is controlled at −5 to 20° C., and preferably 0 to 10° C.; and a temperature of the second reactor is controlled at 0 to 25° C., and preferably 10 to 20° C.

Further, an aqueous methyl urea/hydrochloric acid solution, 2-methyl tetrahydrofuran and an aqueous sodium nitrite solution are respectively and continuously pumped into the first reactor by a first feed pump, a second feed pump and a third feed pump; preferably, the aqueous methyl urea/hydrochloric acid solution includes 1.0 eq of methyl urea, 1.1 to 2.0 eq of 36% concentrated hydrochloric acid, and 2 to 8 v of purified water; and more preferably, 1.4 to 1.6 eq of 36% concentrated hydrochloric acid, and 3 to 5 v of purified water; preferably, the 2-methyl tetrahydrofuran is 10 to 50 v, and more preferably 20 to 30 v; and preferably, the aqueous sodium nitrite solution includes 1.1 to 2.0 eq of sodium nitrate, and 2 to 8 v of water; and more preferably 1.4 to 1.6 eq of sodium nitrite and 3 to 5 v of water.

Further, a residence time of the materials in the first reactor is 5 to 50 min; and preferably 15 to 30 min; and a residence time of the materials in the second reactor is 10 to 60 min, and preferably 20 to 40 min.

Further, an olefin compound and a palladium-containing catalyst are dissolved in tetrahydrofuran and continuously pumped into the second reactor by a fourth feed pump, while an aqueous potassium hydroxide solution is continuously pumped into the second reactor by a fifth feed pump; preferably, the palladium-containing catalyst is palladium acetate; preferably, the olefin compound is 0.1 to 0.5 eq, and more preferably 0.1 to 0.2 eq; the catalyst is 0.0005 to 0.005 eq, and more preferably 0.001 to 0.002 eq; and the tetrahydrofuran is 0.5 to 5 v, and more preferably 2 to 3 v; and preferably, potassium hydroxide in the aqueous potassium hydroxide solution is 2 to 10 eq, and more preferably, the purified water is 5 to 20 V, and more preferably 5 to 10 V.

Further, the method for continuously synthesizing the cyclopropane compound further includes a post-treatment step for the product of the second reactor; preferably, the post-treatment step includes: 1) standing the reaction product of the second reactor to obtain an aqueous phase and an organic phase; 2) extracting the aqueous phase with 5 to 10 v of 2-methyl tetrahydrofuran and combining a product of extracting with the organic phase; 3) drying the combined organic phase with anhydrous sodium sulfate; and 4) condensing the dried organic phase; preferably, the olefin compound has the following structure:

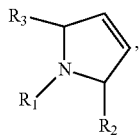

where $R_1$ represents hydrogen, t-butyl oxycarbonyl or carbobenzoxy; $R_2$ represents hydrogen, phenyl, methyl or pyridyl; and $R_3$ represents hydrogen, methyl or ethyl.

According to another aspect of the present disclosure, provided is a device for continuously synthesizing a cyclopropane compound. The device includes a first reactor configured for continuously performing a synthetic reaction of a diazomethane precursor; a separator in communication with the first reactor through a feed inlet of the separator; and a second reactor configured with a feed inlet of the second reactor, the feed inlet of the second reactor being in communication with the feed outlet of the separator.

Further, the first reactor is a helical tube reactor or a continuous stirred tank reactor; and the second reactor is a continuous stirred tank reactor or a column reactor.

Further, the device further includes a first solution tank for containing the aqueous methyl urea/hydrochloric acid solution, a second solution tank for containing 2-methyl tetrahydrofuran, a third solution tank for containing the aqueous sodium nitrite solution, a fourth solution tank for containing tetrahydrofuran dissolved with the olefin compound and the palladium-containing catalyst, and a fifth solution tank for containing the aqueous potassium hydroxide solution; where the first solution tank, the second solution tank and the third solution tank are respectively in communication with the first reactor by a first feed pump, a second feed pump and a third feed pump, and the fourth solution tank and the fifth solution tank are respectively in communication with the fourth feed pump and the fifth feed pump.

The technical solution of the present disclosure may be applied to perform the continuous preparation of a diazomethane precursor (MNU) in a first reactor, and to render the diazomethane precursor to be pumped into a second reactor to in situ participate in the continuous reaction of olefin cyclopropanation, thereby achieving automatic control, decreasing the transfer of high-risk materials, and preventing the risk of pipeline transfer of diazomethane solution, and effectively improving production safety. Moreover, the present disclosure provides a simple device to save equipment investment, and may safely and quantitatively achieve the production of diazomethane and the cyclopropanation reaction of olefins simultaneously.

BRIEF DESCRIPTION OF THE DRAWINGS

Drawings of the description constituting a portion of the present disclosure are used to providing a further understanding of the present disclosure; and schematic examples and specification thereof of the present disclosure are used to explain the present disclosure, and are not intended to limit the present disclosure improperly. In the drawings:

FIG. 1 is a schematic diagram showing a cyclopropanation flow of olefins in one example of the present disclosure.

DETAILED DESCRIPTION OF THE EMBODIMENTS

It should be indicated that the examples of the present application and the features of the examples may be mutually combined without conflict. The present disclosure will be described specifically in combination with the accompanying drawings and examples hereafter.

Directed to a series of technical problems in the prior art, the present disclosure develops a continuous process below: continuously preparing a diazomethane precursor (MNU) in a first reactor (a helical tube reactor or continuous stirred tank reactor), and continuously consuming the diazomethane precursor in a second reactor (a continuous stirred tank reactor or a column reactor) to prepare diazomethane and performing the cyclopropanation reaction of electron-rich monoolefine in situ. In one typical example, the major chemical reaction is as follows:

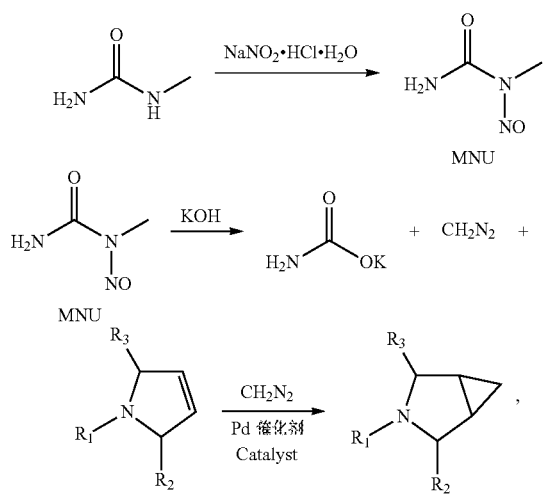

where, $R_1$=hydrogen, t-butyl oxycarbonyl; $R_1$ represents hydrogen, t-butyl oxycarbonyl or carbobenzoxy; $R_2$ represents hydrogen, phenyl, methyl or pyridyl; and $R_3$ represents hydrogen, methyl or ethyl.

According to one typical example of the present disclosure, provided is a method for continuously synthesizing a cyclopropane compound. The method includes the following steps: continuously performing a synthetic reaction of a diazomethane precursor in a first reactor, the reaction product of the first reactor flowing into a separator for stratification, the organic phase obtained by stratification overflowing into a second reactor, continuously consuming the diazomethane precursor in a second reactor to prepare diazomethane and performing an electron-rich monoolefin cyclopropanation reaction in situ so as to obtain the cyclopropane compound.

The technical solution of the present disclosure may be applied to perform the continuous preparation of a diazomethane precursor (MNU) in a first reactor, and to render the diazomethane precursor to be pumped into a second reactor to in situ participate in the continuous reaction of olefin cyclopropanation, thereby achieving automatic control, decreasing the transfer of high-risk materials, and preventing the risk of pipeline transfer of diazomethane solution, and effectively improving production safety. Moreover, the present disclosure has a simple device to save equipment investment, and may safely and quantitatively achieve the production of diazomethane and the cyclopropanation reaction of olefins simultaneously.

The first-stage reaction in the first reactor is two-phase solution reaction, and a helical tube reactor with better leakproofness or a continuous stirred tank reactor may be used; such kind of reactor is beneficial to two-phase reaction. The second-stage reaction in the second reactor is also two-phase solution reaction; the difference is to release gas during reaction, which is against mixing and not suitable for a helical tube reactor. The continuous stirred tank reactor and column reactor may ensure the mixing effect of the reaction solution in case of gas release.

Too low temperature causes precipitates to affect mobility; too high temperature affects the product stability in the first reactor. Therefore, preferably, a temperature in the first reactor is controlled within −5 to 20° C., more preferably 0 to 10° C. A temperature in the second reactor is controlled within 0 to 25° C., more preferably 10 to 20° C.

For the convenience of achieving the continuous automatic generation, in one typical embodiment of the present disclosure, aqueous methyl urea/hydrochloric acid solution, 2-methyl tetrahydrofuran and aqueous sodium nitrite solution are respectively and continuously pumped into the first reactor by a first feed pump, a second feed pump and a third feed pump;

preferably, the aqueous methyl urea/hydrochloric acid solution includes 1.0 eq of methyl urea, 1.1 to 2.0 eq of 36% concentrated hydrochloric acid, and 2 to 8 v of purified water; and more preferably, 1.4 to 1.6 eq of 36% concentrated hydrochloric acid, and 3 to 5 v of purified water (where, v refers to a volume relative to methylurea, for example, when methylurea has a feeding capacity of 1 g, 3 to 5 v purified water denotes 3 to 5 ml feeding capacity of purified water); the above solution not only ensures the solution mobility, but also affects the reaction effect due to too much solvent.

To ensure the smooth and efficient implementation of the reaction, preferably, the 2-methyl tetrahydrofuran is 10 to 50 v, and more preferably 20 to 30 v; and preferably, the aqueous sodium nitrite solution comprises 1.1 to 2.0 eq of sodium nitrate, and 2 to 8 v of water; and more preferably 1.4 to 1.6 eq of sodium nitrite and 3 to 5 v of water.

To make materials reacted well, a residence time of the materials in the first reactor is 5 to 50 min; and preferably 15 to 30 min; and a residence time of the materials in the second reactor is 10 to 60 min, and preferably 20 to 40 min.

In one typical example of the present disclosure, an olefin compound and a palladium-containing catalyst are dissolved in tetrahydrofuran and continuously pumped into the second reactor by a fourth feed pump, while an aqueous potassium hydroxide solution is continuously pumped into the second reactor by a fifth feed pump; preferably, the palladium-containing catalyst is palladium acetate; preferably, the olefin compound is 0.1 to 0.5 eq, and more preferably 0.1 to 0.2 eq; the catalyst is 0.0005 to 0.005 eq, and more preferably 0.001 to 0.002 eq; and the tetrahydrofuran is 0.5 to 5 v, and more preferably 2 to 3 v; and preferably, potassium hydroxide in the aqueous potassium hydroxide solution is 2 to 10 eq, and more preferably, the purified water is 5 to 20 V, and more preferably 5 to 10 V. Therefore, the reaction is performed efficiently.

According to one typical example of the present disclosure, the method for continuously synthesizing the cyclopropane compound further includes a post-treatment step for the product of the second reactor; preferably, the post-treatment step includes: 1) standing the reaction product of the second reactor to be divided into an aqueous phase and an organic phase; 2) extracting the aqueous phase with 5 to 10 v of 2-methyl tetrahydrofuran and combining a product of extracting with the organic phase; 3) drying the combined organic phase with anhydrous sodium sulfate; and 4) condensing the dried organic phase.

According to one typical example of the present disclosure, provided is a device for continuously synthesizing a cyclopropane compound. The device includes a first reactor configured for continuously performing a synthetic reaction of a diazomethane precursor; a separator in communication with the first reactor through a feed inlet of the separator; and a second reactor configured with a feed inlet of the second reactor, the feed inlet of the second reactor is in communication with the feed outlet of the separator. The device may be used to achieve the above technical solution.

Preferably, the first reactor is a helical tube reactor or a continuous stirred tank reactor; and the second reactor is a continuous stirred tank reactor or a column reactor.

Preferably, the device further includes a first solution tank for containing the aqueous methyl urea/hydrochloric acid solution, a second solution tank for containing 2-methyl tetrahydrofuran, a third solution tank for containing the aqueous sodium nitrite solution, a fourth solution tank for containing tetrahydrofuran dissolved with the olefin compound and the palladium-containing catalyst, and a fifth solution tank for containing the aqueous potassium hydroxide solution; wherein the first solution tank, the second solution tank and the third solution tank are respectively in communication with the first reactor by a first feed pump, a second feed pump and a third feed pump, and the fourth solution tank and the fifth solution tank are respectively in communication with the fourth feed pump and the fifth feed pump.

Beneficial effects of the present disclosure will be further described in combination with examples hereafter.

EXAMPLE 1

Olefin compound:

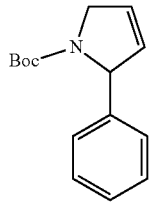 [SMILES: CC(C)(C)OC(=O)N1CC=CC1c1ccccc1]

Continuous reaction: statistics on the speed and reaction parameters of the feed pump are shown in Table 1, and the reaction flow diagram is shown in FIG. 1.

(1) Solution preparation: 370 g purified water and 82.5 g N-methylurea were added to a 2 L conical flask, stirred to be dissolved fully, then 190 g concentrated hydrochloric acid (mass fraction: 36%) was added slowly, and stirred evenly for further use (methyl urea/hydrochloric acid solution). 370 g purified water and 130 g solid sodium nitrite were added to a 1 L conical flask, and stirred to be dissolved fully (aqueous sodium nitrite solution) for further use. 250 ml 2-methyl tetrahydrofuran, 50 g olefin compound (20.38 mmol) and 0.4 g palladium acetate were added to a 1 L conical flask, and stirred to be dissolved fully (aqueous sodium nitrite solution) for further use. 600 g purified water was added to a 1 L conical flask, and 210 g potassium hydroxide was added in batches, then stirred to be dissolved fully (potassium hydroxide solution) for further use.

(2) The temperature of the first reactor 10 was controlled within 0 to 10° C., and the temperature of the second reactor 20 was controlled within 10 to 20° C., and a first feed pump P-1 (methyl urea/hydrochloric acid solution) and a second feed pump P-2 (2-methyl tetrahydrofuran) were simultaneously turned on, later on, a third feed pump P-3 (aqueous sodium nitrite solution) was turned on, such that the three streams of materials were fed into the first reactor 10 simultaneously. The reaction system was fed into a separator 30 from the first reactor 10 for stratification. When an organic phase overflowed into the second reactor 20, a fourth feed pump P-4 (olefin/catalyst solution) and a fifth feed pump P-5 (aqueous potassium hydroxide solution) were turned on, 30 min later, sampling was performed from the second reactor 20 to track the reaction effect. The system in the second reactor 20 was subjected to liquid separation, filtering, concentration and other operations to obtain a cyclopropane product (fed into a reception tank) with a yield of 82%. The whole ramming process lasted about 4 h.

TABLE 1

| Feed pump | Name of materials | Feed quantity (g/min) | Reactor | Volume of materials in reactor (ml) | Temperature (° C.) | Residence time (min) | Typical sample |
|---|---|---|---|---|---|---|---|
| P1 | Methy lurea/HCl aqueous solution | 2.8 | First reactor 1 | About 290 | 0-10 | 20 | Olefin raw material: 1.2% Cyclopropane product: 84.6% |
| P2 | 2-Methyl tetrahydrofuran | 8.5 | | | | | |
| P3 | Aqueous sodium nitrite solution | 2.1 | | | | | |
| P4 | Olefin/catalyst solution | 1.2 | Second reactor 2 | About 500 | 10-20 | 30 | |
| P5 | Aqueous potassium hydroxide solution | 3.5 | | | | | |

COMPARATIVE EXAMPLE 1

Batch Reaction (1) Under nitrogen protection, 135 g purified water and 16.5 g N-methyl urea were added to a 2 L four-necked flask (mechanical stirring), and 26 g solid sodium nitrite were added and stirred to be dissolved fully. 400 g 2-methyl tetrahydrofuran was then added to the four-necked flask, and the system was cooled to 0-10° C.; 38 g concentrated hydrochloric acid (mass fraction: 36%) was dropwise added to the four-necked flask via a constant-pressure dropping funnel slowly, if solid separated out and was not dissolved rapidly during dropwise adding process, the concentrated hydrochloric acid was not added dropwise; after the solid was dissolved, the concentrated hydrochloric acid was added dropwise, and the whole dropping process lasted 1 h. After adding dropwise, the solution was thermally insulated and stirred for 20 to 30 min, and subjected to standing for liquid separation, and the organic phase was further used for the subsequent reaction.

(2) Under nitrogen protection, 50 ml tetrahydrofuran, 10 g olefin compound and 0.4 g palladium acetate were added to another 1 L four-necked flask and, and stirred to be dissolved fully for further use. The aqueous potassium hydroxide solution (42 g potassium hydroxide and 120 g purified water) prepared in advance was added and cooled to 10-20° C., the organic phase in the operation (1) was dropwise added to a 1 L four-necked flask; at the beginning of dropping the blowoff rate was fast, and the feeding speed was reduced, and the dropping speed was controlled in the whole process to achieve slow and smooth blowoff; in later stage, the dropping speed may be increased; at the end of dropping, the system was thermally insulated for 30 min, the sampling was performed to detect the reaction result. The whole dropping process took about 2.5 h. The system was subjected to liquid separation, filtering, concentration and other operations to obtain a cyclopropane product.

Typical sample: olefin raw material: 1.8%, cyclopropane product: 85.2%, yield: 83%.

EXAMPLE 2

Example 2 differed from Example 1 in that the temperature of the first reactor was controlled within 30-35° C. Typical sample: olefin raw material: 18.8%, cyclopropane product: 65.2%, yield: 63%.

EXAMPLE 3

Example 3 differed from Example 1 in that the residence time of the first reactor was 5 min. Typical sample: olefin raw material: 8.2%, cyclopropane product: 75.2%, yield: 73%.

EXAMPLE 4

Example 4 differed from Example 1 in that 2-methyl tetrahydrofuran had a dosage of 50 v. Typical sample: olefin raw material: 5.7%, cyclopropane product: 78.2%, yield: 77%.

EXAMPLE 5

Example 5 differed from Example 1 in that the temperature of the second reactor was controlled within 30-35° C. Typical sample: olefin raw material: 34.8%, cyclopropane product: 52.2%, yield: 47%.

EXAMPLE 6

Example 6 differed from Example 1 in that the residence time of the second reactor was 10 min. Typical sample: olefin raw material: 6.2%, cyclopropane product: 83.9%, yield: 81%.

EXAMPLE 7

Olefin compound:

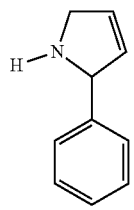 [SMILES: C1=CC(c2ccccc2)NC1]

Continuous reaction was performed, and the embodiment was the same as that in Example 1. Typical sample: olefin raw material: 0.9%, cyclopropane product: 88.2%, yield: 84%.

EXAMPLE 8

Olefin compound:

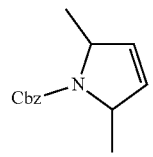 [SMILES: CC1C=CC(C)N1C(=O)OCc1ccccc1]

Continuous reaction was performed, and the embodiment was the same as that in Example 1. Typical sample: olefin raw material: 2.2%, cyclopropane product: 84.2%, yield: 80%.

EXAMPLE 9

Olefin compound:

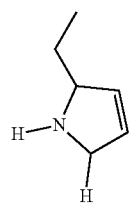

Continuous reaction was performed, and the embodiment was the same as that in Example 1. Typical sample: olefin raw material: 0.7%, cyclopropane product: 86.2%, yield: 84%.

The above mentioned are merely preferred examples of the present disclosure, and are not construed as limiting the present disclosure. A person skilled in the art knows that the present disclosure may have various changes and alterations. Any amendment, equivalent replacement, improvement and the like made within the spirit and principle of the present disclosure should be included within the protection scope of the present disclosure.

What is claimed is:

1. A method for continuously synthesizing a cyclopropane compound comprising the following steps: continuously performing a synthetic reaction of a diazomethane precursor in a first reactor, the reaction product of the first reactor flowing into a separator for stratification, the organic phase obtained by stratification overflowing into a second reactor, continuously consuming the diazomethane precursor in the second reactor to prepare diazomethane and performing an electron-rich monoolefin cyclopropanation reaction on diazomethane in situ so as to obtain the cyclopropane compound;

the method for continuously synthesizing the cyclopropane compound further comprises a post-treatment step for the product of the second reactor;

an electron-rich monoolefin compound and a palladium-containing catalyst are dissolved in tetrahydrofuran and continuously pumped into the second reactor by a fourth feed pump, while an aqueous potassium hydroxide solution is continuously pumped into the second reactor by a fifth feed pump;

the electron-rich monoolefin compound has the following structure:

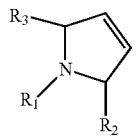

wherein $R_1$ represents hydrogen, t-butyl oxycarbonyl or carbobenzoxy; $R_2$ represents hydrogen, phenyl, methyl or pyridyl; and $R_3$ represents hydrogen, methyl or ethyl.

2. The method of claim 1, wherein the first reactor is a helical tube reactor or a continuous stirred tank reactor; and the second reactor is a continuous stirred tank reactor or a column reactor.

3. The method of claim 1, wherein a temperature of the first reactor is controlled at −5 to 20° C.; and a temperature of the second reaction is controlled at 0 to 25° C.

4. The method of claim 1, wherein an aqueous methyl urea/hydrochloric acid solution, 2-methyl tetrahydrofuran and an aqueous sodium nitrite solution are respectively and continuously pumped into the first reactor by a first feed pump, a second feed pump and a third feed pump.

5. The method of claim 4, wherein a residence time of materials in the first reactor is 5 to 50 min; and a residence time of the materials in the second reactor is 10 to 60 min; wherein the materials comprise the aqueous methyl urea/hydrochloric acid solution, 2-methyl tetrahydrofuran, and the aqueous sodium nitrite solution.

6. The method of claim 3, wherein the temperature of the first reactor is controlled at 0 to 10° C.;
and the temperature of the second reaction is controlled at 10 to 20° C.

7. The method of claim 4, wherein the aqueous methyl urea/hydrochloric acid solution comprises 1.1 to 2.0 eq of methyl urea, 1.1 to 2.0 eq of 36% concentrated hydrochloric acid, and 2 to 8 v of purified water.

8. The method of claim 7, wherein the aqueous methyl urea/hydrochloric acid solution comprises 1.1 to 2.0 eq of methyl urea, 1.4 to 1.6 eq of 36% concentrated hydrochloric acid, and 3 to 5 v of purified water.

9. The method of claim 4, wherein the 2-methyl tetrahydrofuran is 10 to 50 v.

10. The method of claim 4, wherein the aqueous sodium nitrite solution comprises 1.1 to 2.0 eq of sodium nitrate, and 2 to 8 v of water.

11. The method of claim 1, wherein the palladium-containing catalyst is palladium acetate.

12. The method of claim 1, wherein the electron-rich monoolefin compound is 0.1 to 0.5 eq; the catalyst is 0.0005 to 0.005 eq; and the tetrahydrofuran is 0.5 to 5 v.

13. The method of claim 1, wherein potassium hydroxide in the aqueous potassium hydroxide solution is 2 to 10 eq, and the purified water is 5 to 20 V.

14. The method of claim 1, wherein the post-treatment step comprises:
1) standing the reaction product of the second reactor to obtain an aqueous phase and an organic phase;
2) extracting the aqueous phase with 5 to 10 v of 2-methyl tetrahydrofuran and combining a product of extracting with the organic phase;
3) drying the combined organic phase with anhydrous sodium sulfate; and
4) condensing the dried organic phase.

15. The method of claim 5, wherein a residence time of the materials in the first reactor is 15 to 30 min;
and a residence time of the materials in the second reactor is 20 to 40 min.

16. The method of claim 9, wherein the 2-methyl tetrahydrofuran is 20 to 30 v.

17. The method of claim 10, wherein the aqueous sodium nitrite solution comprises 1.4 to 1.6 eq of sodium nitrite and 3 to 5 v of water.

* * * * *